United States Patent [19]

O'Donnell

[11] Patent Number: 5,455,028
[45] Date of Patent: Oct. 3, 1995

[54] **METHOD OF INHIBITING FUNGI BY *BACILLUS LATEROSPORUS***

[76] Inventor: Boyd J. O'Donnell, 31554 Agoura Rd., Unit 6, Westlake Village, Calif. 91361

[21] Appl. No.: 236,701

[22] Filed: Apr. 28, 1994

Related U.S. Application Data

[63] Continuation of Ser. No. 908,631, Jul. 1, 1992, abandoned, which is a continuation of Ser. No. 621,603, Dec. 4, 1990, abandoned.

[51] Int. Cl.⁶ .................................................. C12N 1/20
[52] U.S. Cl. ........................ 424/93.46; 435/252.5
[58] Field of Search ................ 424/93.46; 435/252.5

[56] References Cited

U.S. PATENT DOCUMENTS 5,045,314  7/1991  Bone et al. ................. 424/93.46
5,055,293  10/1991  Aronson et al. .............. 424/93.46

*Primary Examiner*—Marian C. Knode
*Assistant Examiner*—Jean C. Witz
*Attorney, Agent, or Firm*—Lyon & Lyon

[57] ABSTRACT

A method of treating fungal disease in an animal which comprises administering to the animal an effective amount of *Bacillus laterosporus* strain BOD having accession number ATCC 55122 or mutants thereof.

20 Claims, No Drawings

METHOD OF INHIBITING FUNGI BY *BACILLUS LATEROSPORUS*

This is a continuation of Ser. No. 908,631, filed Jul. 1, 1992, now abandoned, which is a continuation of Ser. No. 621,603, filed Dec. 4, 1990, now abandoned.

BACKGROUND OF THE INVENTION

1. Field of the Invention

The present invention relates to a method of inhibiting fungi utilizing *Bacillus laterosporus* strain BOD or mutants thereof.

2. Brief Description of the Background Art

Advances in modern medicine have enabled science to prolong the lives of many individuals with severely debilitating immunologic defenses. Often, patients are predisposed to opportunistic infections because they are receiving corticosteroids, cytotoxic drugs, irradiation, or broad-spectrum antibacterial antibiotics for the management of such conditions as cancer, organ transplant, and other surgical procedures, immunologic disorders, or chronic infections. Particularly susceptible are patients with leukemia, Acquired Immune Deficiency Syndrome (AIDS), Hodgkin's disease, neutropenia, and other hematologic diseases, and endocrinopathies, including diabetes. It has been found that, in general, conditions or treatments which reduce the number or function of phagocytes or impair cell-immediated immunity increase susceptibility to opportunistic mycoses.

Such compromised patients are at risk for systemic candidiasis, cryptococcal meningitis, invasive aspergillosis, and rhinocerebral or thoracic mucormycosis. Avoiding exposure to the agents of these mycosis is almost impossible because they are ubiquitous in the environment or a part of the normal microbial flora. In addition, opportunistic mycosis are life threatening and the most frequently encountered of the systemic fungal infections. In recent years, the incidents of opportunistic mycosis has increased at an alarming rate.

Various species of Candida and Aspergillus can cause other clinical problems, in addition to their role in opportunistic disease. Indeed, any of several of species of the yeast Candida are capable of causing candidiasis. These organisms are members of the normal flora of the skin, mucous membranes, and gastrointestinal tract. Since Candida species colonize the mucosal surfaces of all humans during birth, or shortly thereafter, the risk of indigenous infection is ever present. It is not surprising that candidiasis occurs worldwide and is the most common systemic mycosis. While more than 100 species of Candida exist, several are part of the normal flora and are potential pathogens. However, most infections are caused by *Candida albicans* and *Candida tropicalis*.

Cutaneous candidiasis can be treated with topical antibiotics (such as ketoconazole, nystatin, or miconazole) or chemical solutions (such as gentian violet). The treatment of systemic candidiasis usually requires the administration of such agents as amphotericin B alone or in combination with flucytosine. Unfortunately, many clinical isolets of Candida develop resistance to flucytosine. Consequently, antibiotic therapy for candidiasis is highly variable from one individual to the next and resolution of fungal lesions is primarily associated with improved immunocompetence. Unfortunately, both responses are often only temporary.

Prophylaxis of patients at risk for systemic candidiasis has been attempted using oral ketoconazole or nystatin, or a low dose or short course of amphotericin B, often in combination with antibacterial antibiotics. While controlled studies have usually resulted in lower resistances of candidiasis in treated patients, a significant and standard regimen has not been established. Thus, there exists a significant need for compositions which can inhibit the proliferation of Candida, but do not have the often severe side effects associated with existing antibiotics. The present invention provides a therapeutic composition which has these characteristics.

SUMMARY OF THE INVENTION

This invention involves compositions which contain a microorganism which can inhibit fungi. This organism, a *Bacillus laterosporus* strain designated BOD, has the identifying characteristics of the organism having ATCC Accession Number ATCC 55122.

BRIEF DESCRIPTION OF THE PREFERRED EMBODIMENT

The method of the present invention is highly desirable in that the organism of the invention is non-pathogenic and should thereby render unlikely the occurrence of any deleterious effects due to its use. Also of significance is the fact that the method of treating fungal disease according to the invention does not necessitate the supplemental use of antibiotics and relies rather upon "natural" mechanisms of controlling disease. This aspect of the invention is important in the face of growing public concern over the use of antibiotics, especially their presence in meat, and the effect that these antibiotics may have on the health of the general population.

The organism of the invention was isolated from soil. The organism effective in inhibiting fungi which can cause disease is *Bacillus laterosporus* strain BOD having accession number ATCC 55122 or effective mutants thereof. Such mutants are considered equivalents to the parent strain.

It is well known to those of ordinary skill in the art that spontaneous mutation is a common occurrence in microorganisms and that mutations can be intentionally produced by a variety of known procedures. For example, mutants can be induced using chemical, radioactive, and recombinant techniques. As shown in Table 1, chemical mutagens can be divided into four main groups based upon their activity.

TABLE 1

| CHEMICAL MUTAGENS | |
|---|---|
| ACTIVITY | EXAMPLES |
| Based Analogs | 5-bromouracil, 2-aminopyrine |
| Deaminating Agents | nitrous acid, hydroxylamine |
| Alkylating Agents | ethyl ethanesulfonate, nitrosoguanidine |
| Acridine Derivatives | acridine orange, ethidium bromide |

Any of these can be used in the present invention to produce mutations.

Radiation induced mutations can be caused by such agents as ultraviolet light, and x-rays. The primary mechanism by which mutations may be caused results from excision or post replication repair by recombination.

Additionally, mutations can also be produced by recombinant techniques using restriction endonucleases. Use of this technique is especially valuable to allow the deletion or insertion of large DNA fragments.

Regardless of the manner in which the mutations are induced, the critical issue is that the mutants function as described for the parent strain. In other words, the present invention includes mutations resulting in such minor changes as, for example, minor taxonomic alterations such as the fermentation of certain sugars.

The diseases for which the present invention is effective can be any in which the underlying etiology is characterized as fungal. Alternatively, the present invention is also useful in animals where the normal gut flora has been eliminated or unbalanced as, for example, following severe viral gastroenteritis or high dose antibiotic therapy in order to aid in the restoration of the normal gut flora and prevent colonization by opportunistic pathogens. The term "animal" encompasses humans as well as non-humans.

Protection from fungal disease can most easily be accomplished by feeding *B. laterosporus* strain BOD having accession number ATCC 55122, or compositions containing this organism, to the animal in which protection is sought.

Compositions may be in a liquid, lyophilized, or gel form. In solid dosage forms, the composition may comprise the organism of the invention together with a pharmaceutical carrier. The pharmaceutical carrier may be in the nature of an aqueous or nonaqueous liquid or a solid. In solid dosage forms, the composition may contain such inert diluents as sucrose, lactose, starch, or vermiculite as well as a lubricating agent. These lubricating agents aid in the passage of the compositions through the gut. In the case of capsules, tablets and pills, the unit dosage forms may also comprise buffering agents. Other forms of oral administration may also be prepared with an enteric coating which would prevent dissolution of the composition until reaching the intestines.

Compositions according to this invention would contain about $10^4$–$10^{12}$ viable organisms/gm, more preferably about $10^4$–$10^8$ viable organisms/gm, most preferably about $10^5$–$10^7$ viable organisms/gm.

Liquid dosage forms for oral administration may comprise dissolving or suspending a composition containing the organism of the invention in a potable liquid, such as pharmaceutically pure water. Alternatively, liquid or dry oral administration forms can comprise an enterically coated capsule containing the dosage form. Suitable forms include emulsions, suspensions, solutions, syrups, and elixirs containing inert diluents commonly used in the art, such as purified water, sugars, polysaccharides, silicate gels, gelatin, or an alcohol. These inert diluents do not actively participate in the therapeutic effect of the invention. Besides the inert diluents, such compositions can also include wetting agents, emulsifying and suspending agents, and sweetening, flavoring, and perfuming agents.

The dose ranges for a given animal would vary depending on the weight and concomitant administration of antibiotics. The dose could be administered as either single or multiple dosages and would contain about $10^4$–$10^{12}$ viable organisms/dose, more preferably about $10^4$–$10^8$ viable organisms/dose, most preferably about $10^5$–$10^7$ viable organisms/dose.

Alternatively, an animal can be administered the equivalent of these concentrations or organisms where the values are expressed by some other measurement such as, for example, total protein concentration or in cell fragment concentration.

The invention also relates to a method for preparing a medicament or pharmaceutical composition comprising the components of the invention, the medicament being used for the treatment of fungal disease.

Those of ordinary skill in the art will know of other suitable diluents and dosage forms, or will be able to ascertain such, using routine experimentation. Further, the administration of the various compositions can be carried out using standard techniques common to those of ordinary skill in the art.

The above disclosure generally describes the present invention. A more complete understanding can be obtained by reference to the following specific example which is provided herein for purposes of illustration only and is not intended to be limiting unless otherwise specified.

EXAMPLE 1

GROWTH AND MAINTENANCE OF *Bacillus laterosporus*

*Bacillus laterosporus* strain BOD was grown and maintained on Trypticase Soy Agar (TSA) (BBL). Slants were streaked, incubated at 35° C. for 24–72 hours and then stored at 8° C. The slants of the Bacillus were transferred to fresh slants every 30 days. *Bacillus laterosporus* was inoculated from TSA slants into sterile Trypticase Soy Broth (TSB) (BBL). The broth was incubated at 35° C., preferably with slow agitation, for 24–72 hours. After 24–72 hours, a plate count was done on the broth culture to determine the growth level. The broth culture was then diluted 500-fold with sterile filtered deionized water. A plate count was done on each batch to determine the level of *Bacillus laterosporus* in the batch and to determine the purity of the batch. The product was filled into containers. Initial, intermediate, and end samples of the run were plated to determine the purity of the filled batch. *Bacillus laterosporus* was maintained as above. The aerobic plate count was determined to be $1.8 \times 10^6$ cells/g.

If desired, *Bacillus laterosporus* cultures can be freeze dried for more convenient use. To provide a freeze dried culture, the bacteria were grown in a sterile solution of ½ strength TSB to which an equal amount of malto-dextrin or cellulose binder was added. The solution was inoculated and incubated as above. The solution was freeze dried. The freeze dried product is then checked for bacterial plate count, then diluted so that the plate count per capsule will be about $6.0 \times 10^5$ to about $7.0 \times 10^5$. The composition containing the organisms is then filled into No. 1 capsules.

EXAMPLE 2

ANTIMICROBIAL PRESERVATIVE EFFECTIVENESS TESTING

The ability of *Bacillus laterosporus* strain BOD and *Bacillus laterosporus* ATCC 31932 were tested for their activity as antimicrobial preservatives as described in the modified United States Pharmacopeia. The USP Challenge Test utilized the organism of the invention which was present in the form of a liquid sample of the product containing viable *Bacillus laterosporus* strain BOD whereas the *Bacillus laterosporus* ATCC 31932 was tested in the form of a 200 ml 24 hour tryptic soy broth culture on second successive transfer. The results of the USP Challenge Test are shown in Table 2.

TABLE 2

USP CHALLENGE TESTING OF *Bacillus laterosporus*

| B. laterosporus | Initial Inoculum | Candida albicans (ATCC 10231)[a] | | | |
|---|---|---|---|---|---|
| | | 7 Days | 14 days | 21 days | 28 days |
| Strain BOD | $10^6$ | $3.6 \times 10^3$ $(3.6)^b$ | $2.6 \times 10^4$ $(2.6)$ | $8 \times 10^3$ $(0.8)$ | $1.9 \times 10^3$ $(0.19)$ |
| ATCC 31932 | $5.2 \times 10^3$ | $1.1 \times 10^6$ $(>10^3)$ | $6.2 \times 10^5$ $(>10^3)$ | $6.4 \times 10^6$ $(>10^3)$ | $7.1 \times 10^6$ $(>10^3)$ |

[a] colony counts at various times after inoculation
[b] percent growth compared to initial inoculum This data shows that the product containing strain BOD meets the criteria set forth for preservative effectiveness.

*Bacillus laterosporus* strain BOD has been deposited for 30 years at the American Type Culture Collection (ATCC) in Rockville, Md. and assigned Accession Number ATCC 55122.

The present invention is not to be limited in scope by the organism deposited, since the deposited embodiment is intended to serve as a single illustration of one aspect of the invention and any organism which is functionally equivalent is within the scope of this invention. The deposit of material does not constitute an admission that the written description contained herein is inadequate to enable the practice of any aspect of the invention, including the best mode, nor is the deposit to be construed as limiting the scope of the claims to the specific illustrations that they represent. In point of fact, there will become apparent to those of skill in the art that there are modifications of the invention, in addition to those shown and described herein, which are readily possible. It is intended that such modifications fall within the scope of the appended claims.

I claim:

1. A fungal inhibiting composition comprising an effective amount of a biologically pure culture of *Bacillus laterosporus* BOD having all the identifying characteristics of ATCC Accession Number 55122.

2. The composition of claim 1, further comprising a pharmaceutical carrier.

3. The composition of claim 2, wherein the pharmaceutical carrier is a liquid or a solid.

4. The composition of claim 3, wherein the liquid carrier is aqueous or non-aqueous.

5. The composition of claim 4 wherein the composition is contained in an enteric coating.

6. The composition of claim 3, wherein the solid carrier is an inert diluent.

7. The composition of claim 6, wherein the inert diluent is malto-dextrin or a cellulose binder.

8. The composition of claim 6, wherein the inert diluent contains a lubricating agent.

9. The composition of claim 6 wherein the composition is contained in an enteric coating.

10. The composition of claim 1, wherein the composition has been formulated for enteral administration.

11. The composition of claim 1, wherein the composition contains about $10^4$–$10^{12}$ viable organisms/gm.

12. The composition of claim 1, wherein the composition contains about $10^4$–$10^8$ viable organisms/gm.

13. The composition of claim 1, wherein the composition contains about $10^5$–$10^7$ viable organisms/gm.

14. A method for treating a fungal disease in an animal which comprises administering to the animal an effective amount of a fungal inhibiting composition comprising a biologically pure culture of *Bacillus laterosporus* BOD having all the identifying characteristics of ATCC Accession Number 55122.

15. The method of claim 14, wherein the composition is administered enterally.

16. The method of claim 15, wherein the composition is in a liquid lyophilizate bolus form.

17. The method of claim 14, wherein the composition of *Bacillus laterosporus* BOD contains about $10^4$–$10^{12}$ organisms/gm.

18. The method of claim 17, wherein the composition of *Bacillus laterosporus* BOD contains about $10^4$–$10^8$ organisms/gm.

19. The method of claim 18, wherein the composition of *Bacillus laterosporus* BOD contains about $10^5$–$10^7$ organisms/gm.

20. A biologically pure culture of *Bacillus laterosporus* BOD having all the identifying characteristics of ATCC Accession Number 55122.

* * * * *